United States Patent [19]

Mauck et al.

[11] Patent Number: 4,786,605

[45] Date of Patent: Nov. 22, 1988

[54] ANALYTICAL METHOD AND ELEMENT FOR PROTEIN ASSAY

[75] Inventors: John C. Mauck, Rochester; Harold C. Warren, III, Rush, both of N.Y.

[73] Assignee: Eastman Kodak Company, Rochester, N.Y.

[21] Appl. No.: 64,640

[22] Filed: Jun. 22, 1987

[51] Int. Cl.$^4$ .................. G01N 33/00; G01N 21/00; G01N 1/48

[52] U.S. Cl. .................. 436/86; 436/164; 422/56; 422/57

[58] Field of Search .............. 422/56, 57, 58; 436/86, 436/82, 88, 164, 161

[56] References Cited

U.S. PATENT DOCUMENTS

| | | | |
|---|---|---|---|
| 3,992,158 | 11/1976 | Przybylowicz et al. | 422/57 |
| 4,042,335 | 8/1977 | Clément | 422/56 |
| 4,132,528 | 1/1979 | Eikenberry et al. | 23/230 |
| 4,248,829 | 2/1981 | Kitajima et al. | 422/57 |

Primary Examiner—Michael S. Marcus
Assistant Examiner—Lyle Alfandary-Alexander
Attorney, Agent, or Firm—John R. Everett

[57] ABSTRACT

There is disclosed a method for quantitatively determining protein, comprising the steps of:

(a) providing a sample of the protein in an aqueous medium;

(b) providing an aqueous medium having a pH in excess of 12 and comprising
 (i) a cupric salt and a pyridyl-azo dye; or
 (ii) a preformed cupric-pyridylazo dye complex;

(c) combining the aqueous mediums of a) and b) thereby providing a color having an intensity which is inversely proportional to the amount of unreacted dye present in the combined mediums; and (d) determining the quantity of protein present in the sample colorimetrically.

The method can be used with a multilayer dry analytical element.

15 Claims, No Drawings 4,786,605

ANALYTICAL METHOD AND ELEMENT FOR PROTEIN ASSAY

FIELD OF THE INVENTION

The present invention relates to clinical chemistry. In particular, it relates to methods and elements for determining protein in aqueous liquids.

BACKGROUND OF THE INVENTION

Methods for assaying proteins in aqueous liquids such as biological liquids (blood, serum and urine) are known. Both wet and dry methods are known. Such assays are carried out for a variety of reasons. For example, the knowledge of protein levels in human serum and urine is important in the diagnosis of such conditions as viral or bacterial meningitis.

Wet methods refer to those methods in which the clinical reagents are first dissolved or suspended in a liquid aqueous vehicle. Dry chemical methods have reference to chemical methods which are performed using reagent composition incorporated in various substantially "dry-to-the-touch" elements. Examples of such elements include "dip and read" test strips and multi-zone analytical test elements. The latter elements are disclosed for example, in U.S. Pat. No. 4,132,528.

The chemical reaction used extensively in both wet and dry protein assay methods is the "biuret" reaction. The general reaction is described in "Determination of Serum Protein by Means of the Biuret Reaction" prepared by A. G. Gornall et al appeared in *Journal of Biology Chemistry*, Vol. 177, page 751 (1949).

In general the biuret reaction involves a "biuret" reagent which contains the chelated cupric form of copper and a base composition of sufficient strength to provide a pH in excess of about 12). When protein in an aqueous liquid such as serum interacts with the biuret reagent, a reaction between the cupric form of copper and the protein occurs to produce a violet color. The color intensity is directly proportional to the protein content of the serum. Thus, the protein level can be measured by well known colorimetric analytical techniques.

In the element of U.S. Pat. No. 4,132,528 the analytical element is a multi-zone analytical element. The element comprises a spreading zone or layer in fluid contact with a reagent zone or layer. The reagent layer or zone is coated on a support such as polyethylene terephthalate. The biuret composition is included in the reagent zone. The reagent zone also includes an alkaline producing composition of sufficient concentration to maintain a pH in excess of 12. This element, while extremely useful and convenient, has the disadvantage that it has low sensitivity in that it cannot detect protein level at 100 mg/dl or below.

SUMMARY OF THE INVENTION

The present invention provides a method for the quantitative determination of protein, comprising the steps of:

(a) providing a sample of the protein in an aqueous medium;

(b) providing an aqueous medium having a pH in excess of 12 and comprising
 (i) a cupric salt and a pyridyl-azo dye or
 (ii) a preformed cupric-pyridyl-azo dye complex; and (c) combining the aqueous mediums of (a) and (b) thereby forming a color having an intensity which is inversely proportional to the amount of unreacted dye present in the combined mediums; and (d) determining the quantity of protein present in the sample colorimetrically.

The analytical method provided by this invention for determining protein is more sensitive then analytical methods based on the biuret reaction.

The foregoing analytical method can be incorporated into dry chemical techniques. Thus, the present invention also provides an analytical element for determination of protein in an aqueous medium comprising an absorbent material which contains (i) a cupric salt and a pyridyl-azo dye or a preformed cupric-pyridyl-azo dye complex and (ii) a composition capable of establishing a pH in excess of 12 when the absorbent material is contacted with an aqueous medium.

A particularly useful analytical element of the invention is a multilayer element comprising (i) a support bearing, (ii) a spreading layer, (iii) one or two reagent layers in fluid contact with the spreading layer; and (iv) a cupric salt and a pyridyl-azo dye or a preformed cupric-pyridyl-azo dye complex and a base composition capable of establishing a pH in excess of 12; wherein the salt and the dye are in the same or different layers.

DETAILED DESCRIPTION OF THE INVENTION

This invention is based upon the capability of protein to displace $Cu^{+2}$ from a cupric-pyridyl-azo dye complex. Cupric ion ($Cu^{+2}$) is complexed with a pyridyl-azo dye in an alkaline environment having a pH in excess of 12. The complex, in solution, has an absorption curve which is shifted to a higher wavelength relative to the absorption curve of the dye alone. When protein is added to the solution the cupric ion is removed from the complex by the protein. This causes a net shift to a lower wavelength from the $Cu^{+2}$-dye complex absorption curve to the absorption curve of the dye alone. If the absorption density is monitored at the peak of the $Cu^{+2}$-dye complex concentration, addition of protein causes a loss of density which is proportional to the concentration of protein added to the solution. This means that in aqueous solutions comprising a $Cu^{+2}$ ion, protein and a pyridyl-azo dye, the $Cu^{+2}$ has a greater affinity for the protein than for the pyridyl-azo dye. Therefore, in compositions in which both the $Cu^{+2}$ ion and the dye concentrations are known, the concentration of protein in an unknown aqueous liquid can be determined colorimetrically.

Representative pyridyl-azo dyes useful in the present invention have the structure

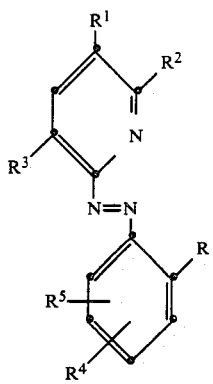

wherein

R represents an electron donor such as OH, NH$_2$, dialkylamino wherein alkyl contains from 1 to 6 carbon atoms, COO$^-$, etc.;

R$^1$ represents H, OH, NH$_2$, dialkylamino wherein alkyl is the same as defined for R;

R$^2$ represents H, NH$_2$, or OH,;

R$^3$ represents H, C$_6$H$_5$NHSO$_2$, CH$_3$SO$_2$, Cl, Br, Cn, etc.; and

R$^4$ represents H, (CH$_3$)$_2$NSO$_2$, OH, NO$_2$, dimethylmino etc., or R$^4$ together with R$^5$ and the carbon atoms to which they are attached form a fused phenyl group.

Examples of dyes having the above structure include

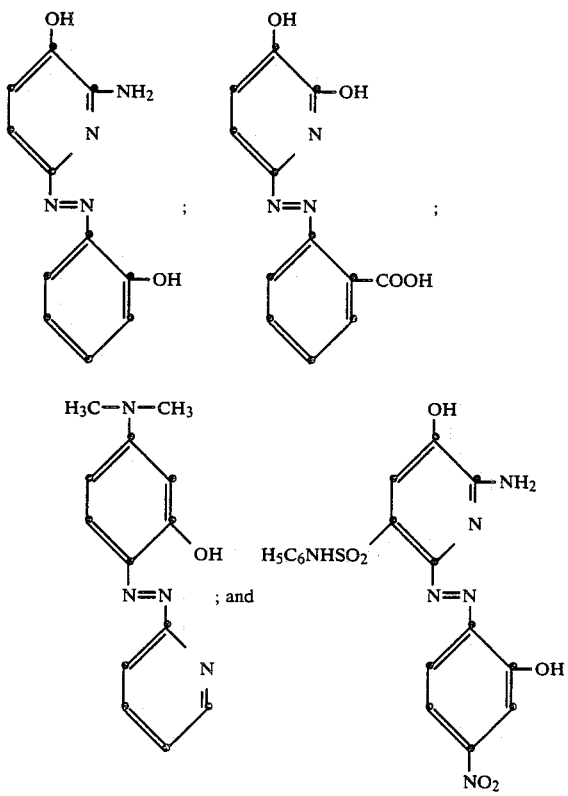

The dyes are prepared according to procedures described in U.S. Pat. No. 4,195,994.

The present invention provides a qualitative and quantitative determination of protein in aqueous liquids. The invention can be used to assay biological fluids of either animals or humans, but preferably of humans. Such fluids include, but are not limited to, whole blood, plasma, sera, lymph, bile, urine, spinal fluid, sputum, perspiration and the like as well as stool secretions. It is also possible to assay fluid preparations of human or animal tissue such as skeletal muscle, heart, kidney, lungs, brains, bone marrow, skin and the like.

A partial list of representative cupric salts includes cupric perchlorate, cupric sulfate, cupric acetate, cupric butyrate, cupric bromate, cupric chlorate, cupric bromide, cupric chloride, cupric fluoride, cupric dichromate, cupric formate, cupric iodate, cupric lactate, cupric orthophosphate, cupric laurate, cupric salicylate, cupric nitrate, cupric tartrate, cupric sulfate and cupric oxalate. An especially useful salt is cupric-ethylacetoacetate.

Cupric salt and dye concentrations in the range of 0.02 to 0.3 g/m$^2$ in the elements of the invention have proved to be useful, considering the expected concentration of protein in an unknown sample.

Compounds which have been found useful in establishing a pH in excess of 12 include strong basic compounds such as lithium hydroxide, calcium hydroxide, mixtures thereof, and the like. Particularly preferred is lithium hydroxide which may be readily coated from aqueous coating dopes and which, when admixed with an appropriate alkaline protective polymer such as described in U.S. Pat. No. 4,132,528, have been found to be remarkably stable and retentive of a high degree of alkalinity. Of course, other substantially sodium-free strongly basic compounds can also be used within the scope of the present invention.

As stated before, the method of this invention is also practiced with a dry analytical element. The simplest element can be composed of an absorbent carrier material, for example, a thin sheet of a self-supporting absorbent or bibulous material, such as filter paper or strips, which contains the analytical composition of this invention. The element can be divided into two or more discrete zones with different reagents incorporated into individual zones of the carrier material. Such elements are known in the art as test strips, diagnostic elements, dip sticks or diagnostic agents.

Useful absorbent carrier materials are insoluble and maintain their structural integrity when exposed to water or biological fluids such as whole blood or serum. Useful elements can be prepared from paper, porous particulate structures, porous polymeric films, cellulose, glass fibers, woven and nonwoven fabrics (synthetic and nonsynthetic) and the like. Useful materials and procedures for making such elements are well known in the art as exemplified in U.S. Pat. Nos. 3,092,465; 3,802,842; 3,915,647; 3,917,453; 3,936,357; 4,248,829; 4,255,384; 4,270,920; and 4,312,834.

Preferably, the absorbent carrier material of the dry analytical element of this invention is a porous spreading zone. This zone can be self-supporting (that is, composed of a material rigid enough to maintin its integrity), but preferably it is carried on a separate support. Such a support can be any suitable dimensionally stable, and preferably, nonporous and transparent (that is, radiation transmissive) material which transmits electromagnetic radiation of a wavelength between about 200 and about 900 nm. A support of choice for a particular element should be compatible with the reflectance spectroscopy mode of colorimetry. Useful supports can be prepared from paper, metal foils, polystyrene, polyesters, polycarbonates, cellulose esters and others known in the art.

The porous spreading zone can be prepared from any suitable fibrous or non-fibrous material or mixtures of either or both. The void volume and average pore size of this zone can be varied depending upon the use intended.

Useful spreading zones can be prepared using fibrous materials, either mixed with a suitable binder material or woven into a fabric, as described in U.S. Pat. No. 4,292,272, polymeric compositions or particulate materials, for example, blush polymers are described in U.S. Pat. No. 3,992,158, beads bound together with or without binding adhesives, as described in U.S. Pat. Nos. 4,258,001 and 4,430,436 and Japanese Patent Publication 57(1982)-101760. It is desirable that the spreading zone be isotropically porous, meaning that the porosity is the same in each direction in the zone as caused by interconnected spaces or pores between particles, fibers or polymeric strands.

The elements can have two or more discrete zones, either in the same layer or superimposed. At least one of the zones is preferably a porous spreading zone. The other zones can be reagent zones or registration zones as those zones are known in the art, additional spreading zones, radiation-blocking or filter zones, subbing zones or barrier zones. The zones are generally in fluid contact with each other, meaning that fluids, reagents and reaction products (for example, color dyes) can pass to be transported between superposed regions of adjacent zones. In other words, when the element is contacted with fluid, all reagents of the analytical composition of this invention become mixed and can readily move within the element as a composition. Preferably, each zone is a separately coated layer, although two or more zones can be separate areas in a single layer of the element. Besides the references noted above, suitable element components are described also, for example, in U.S. Pat. Nos. 4,042,335; 4,132,528 and 4,144,306.

The preferred multilayer elements are placed in use by applying to the element a sample of liquid under analysis. Typically, an element will be formed such that an applied sample will contact a spreading layer prior to the reagent layer and will first contact such spreading layer at its surface furthest removed from such reagent layer. Because analytical accuracy of the present elements is not substantially diminished by variations in the volume of applied samples, sample application by hand or machine is acceptable. For reasons of convenience in detecting an analytical result, however, reasonable consistency in sample volume may be desirable.

In a typical analytical procedure using the elements, which could be manual or automated, the element is taken from a supply roll, chip packet or other source and positioned to receive a free drop, contact spot or other form of liquid sample, such as from an appropriate dispenser. After sample application, and desirably after the liquid sample has been taken up by a spreading layer, the element is exposed to any conditioning, such as heating, humidification or the like, that may be desirable to quicken or otherwise facilitate obtaining any test result.

After the analytical result is obtained as a detectable change, it is measured, usually by passing the element through a zone in which suitable apparatus for reflection or transmission spectrophotometry is provided. Such apparatus would serve to direct a beam of energy, such as light, through the support and the reagent layer. The light would then be reflected, such as from an opacifying agent in the spreading or a radiation-blocking layer in the element, back to a detecting means or would pass through the element to a detector, in the case of transmission detection. In a preferred mode, the analytical result is detected in a region of the element totally within the region in which such result is produced. Generally, electromagnetic radiation in the range of from about 400 to about 700 nm has been found useful for such measurements, although any radiation to which the element is permeable and which is capable of quantifying the detectable change produced in the element can be used. Various calibration techniques can be used to provide a control for the analysis. As one example, a sample of analyte standard solution can be applied adjacent to the area where the drop of sample is placed in order to permit the use of differential measurements in the analysis.

The elements of this invention can also contain one or more other addenda commonly put in the elements for various manufacturing or operational advantages. Such addenda include surfactants, buffers, solvents, hardeners and other materials known in the art.

The following examples are presented to further clarify the invention.

EXAMPLE 1

The method of this invention was evaluated with a multi-layer analytical element having a pyridyl-azo dye in the reagent layer and a $Cu^{+2}$ salt in the spreading layer. The element was prepared as described in U.S. Pat. No. 4,357,363.

| | Cerebrospinal Fluid Protein Element Structure | | |
|---|---|---|---|
| | | $g/m^2$ | Useful Range $g/m^2$ |
| Spreading Layer | Poly[(m + p)-vinyl toulene (64:36)-co-t-butyl styrene-co-methacrylic acid] (20-40μ) | 160 | 30-240 |
| | Poly(N—isopropyl acrylamide) (Binder) | 0.54 | 0.15-1.1 |
| | PVP K-90 (Binder) | 9 | 3-20 |
| | TX-100 (Surfactant) | 1 | 0.1-3 |
| | $Cu^{+2}$—(Ethylacetoacetate)$_2$ (copper source for dye) | 0.1 | 0.02-0.3 |
| Reagent Layer | Poly(acrylamide-co- N—vinyl-2-pyrolidone) (50/50) (Binder) | 10 | 3-20 |
| | LiOH (Buffer) | 3 | 1-6 |
| | Zonyl FSN (Surfactant) | 0.1 | 0.02-0.5 |
| | 2-amino-3-hydroxy-5-$N_1$—phenyl sulfanyl-6-[$2^1$-hydroxy-$4^1$-nitro]phenylazo-pyridine | 0.145 | 0.02-0.3 |

The above element was evaluated using a number of different aqueous liquids containing known quantities of protein. In Table I the results of this evaluation are tabulated.

TABLE I

| Reference Value (mg/dl) | No. of Tests | $D_R$ | Mean Predicted Value (mg/dl) | Precision (Percent CV) |
|---|---|---|---|---|
| 40.00 | 9 | 1.535 | 33.46 | 4.36 |
| 80.00 | 9 | 1.457 | 84.09 | 4.89 |
| 100.00 | 10 | 1.395 | 102.53 | 4.16 |
| 200.00 | 9 | 1.208 | 197.99 | 2.40 |
| 300.00 | 10 | 1.089 | 300.22 | 4.61 |

$D_R$ = reflectance density at 670 nm
Predicted Value = protein concentration as determined by the results of calibration against the reference value
CV = coefficient of variation The above results show that the element has good dynamic range and precision in determining protein levels. The standard deviation at 40 mg/dl was 1.5 mg/dl. The above data also shows that the sensitivity of the element in the normal range is 0.915 $D_R$/100 mg/dl. The normal range is the level of protein found in the serum of normal subjects. That range is 15 to 45 mg/dl. This is about 30 times greater than the sensitivity of the prior art biuret technique for determining total protein.

In the assays carried out and evaluated in Table I, all colorimetric readings were made five minutes after the sample in each test was first spotted on the spreading layer of the element. This five minute incubation period was found to be sufficient time for the chemical reactions involved and the resultant color density to reach a sufficiently stable state to allow precise and accurate measurement of protein levels in each sample tested.

EXAMPLE 2

Assays were also carried out on the element of example 1 with human serum albumin having a molecular weight of 60,000 and human gamma gobulin with a molecular weight of 150,000. It was found that both proteins give the same change in reflection density for each mg/dl of protein. This means that proteins of different molecular weights give the same reactivity. Therefore, the method and analytical elements of this invention will measure the level of all proteins with the same precision and accuracy.

The invention has been described in detail with particular reference to preferred embodiments thereof, but it will be understood that variations and modifications can be effected within the spirit and scope of the invention.

We claim:

1. A method for quantitatively determining protein, comprising the steps of:
   (a) providing a sample of the protein in an aqueous medium;
   (b) providing an aqueous medium having a pH in excess of 12 and comprising
      (i) a cupric salt and a pyridyl-azo dye; or
      (ii) a preformed cupric-pyridyl-azo dye complex;
   (c) combining the aqueous mediums of (a) and (b) thereby forming a color having an intensity which is inversely proportional to the amount of unreacted dye present in the combined mediums; and
   (d) determining the quantity of protein present in the sample colorimetrically.

2. The method of claim 1 wherein the dye has the structure

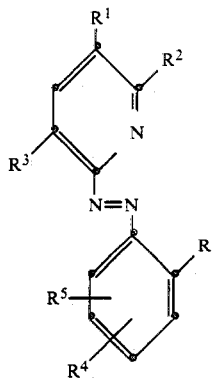

wherein
   R represents —OH, NH$_2$ or dialkylamino;
   R$^1$ represents H, OH, NH$_2$ or dialkylamino;
   R$^2$ represents H, NH$_2$, or OH;
   R$^3$ represents H or C$_6$H$_5$NHSO$_2$, CH$_3$SO$_2$, Cl, Br, or CN;
   R$^4$ represents H, (CH$_3$)$_2$NSO$_2$ or NO$_2$ or R$^4$, together with R$^5$ and the carbon atoms to which they are attached form a fused phenyl group.

3. The method of claim 2 wherein R represents OH, NH$_2$ or COOH.

4. The method of claim 1 or 2 wherein the dye is

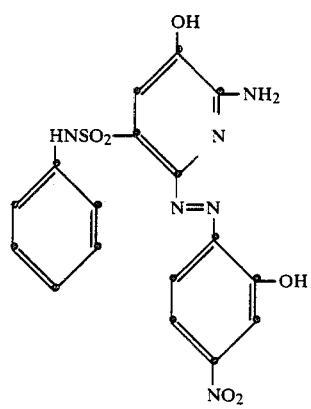

and the cupric salt is Cu$^{+2}$(ethylacetoacetate)$_2$.

5. The method of claim 1 wherein the colorimetric measurement is taken at 670 nanometers.

6. An analytical element for determination of protein in an aqueous medium comprising an absorbent material which contains
   (i) a cupric salt and a pyridyl-azo dye or a preformed cupric-pyridyl-azo dye complex and
   (ii) a base composition capable of establishing a pH in excess of 12 when the absorbent material is contacted with an aqueous medium.

7. A multilayer analytical element for determination of protein in an aqueous medium, comprising
   (i) a support bearing,
   (ii) a spreading layer,
   (iii) one or two reagent layers in fluid contact with the spreading layer; and
   (iv) a cupric salt, a pyridyl-azo dye or a preformed cupric-pyridyl-azo dye complex and a base composition capable of establishing a pH in excess of 12;
   wherein the salt and the dye are in the same or different layers.

8. The element of claim 6 or 7 wherein the pyridyl-azo dye has the structure

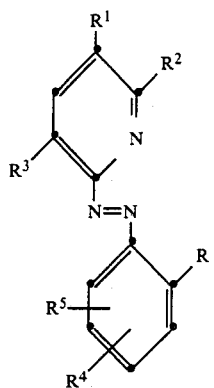

wherein

R represents an electron donor;

$R^1$ represents H, OH, $NH_2$ or dialkylamino;

$R^2$ represents H, $NH_2$, or OH;

$R^3$ represents H or $C_6H_5NHSO_2$, $CH_3SO_2$, Cl, Br, or CN;

$R^4$ represents H, $(CH_3)_2NSO_2$ or $NO_2$, dimethylamino or $R^4$, together with $R^5$ and the carbon atoms to which they are attached form a fused phenyl group.

9. The element of claim 6 or 7 wherein the cupric salt is $Cu^{+2}(ethylacetoacetate)_2$ and the dye is

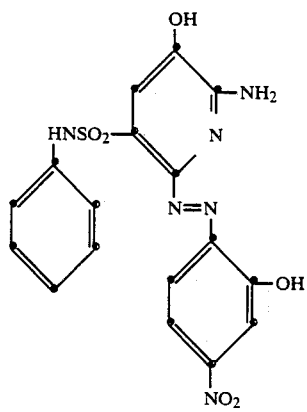

10. The element of claim 7 wherein the cupric salt is in the spreading layer and the pyridyl-azo dye is in the reagent layer.

11. The element of claim 7 wherein the dye and the cupric salt or a preformed cupric-pyridyl-azo dye complex are in the reagent layer.

12. The element of claim 6 or 7 wherein the base composition is a mixture of lithium hydroxide and poly(acrylamide-co-N-vinyl-2-pyrolidone) in weight ratio of 50:1.

13. The element of claim 6 or 7 wherein the copper salt is $Cu^{+2}(ethylacetoacetate)_2$; the dye has the structure

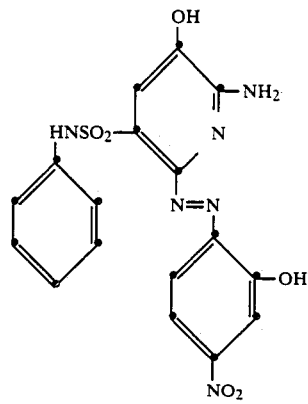

and the base composition comprises lithium hydroxide, and poly(acrylamide-co-N-vinyl-2-pyrolidone) weight ratio 50:1.

14. The element of claim 6 or 7 comprising 0.02 to 0.3 g/m² of the copper salt and 0.02 to 0.3 g/m² of the pyridyl-azo dye.

15. A method for the quantitative analysis of proteins in an aqueous liquid sample which comprises
    (a) providing an analytical element for the determination of protein in an aqueous medium comprising an absorbent material which contains
        (i) a support bearing,
        (ii) a spreading layer,
        (iii) a reagent layer in fluid contact with the spreading layer, and comprising a cupric salt and a pyridyl-azo dye or a preformedd cupric-pyridyl-azo dye complex; and
    (b) applying a portion of the sample to the spreading layer of the analytical element,
    (c) colorimetrically determining, after a predetermined time, the quantity of protein in the sample wherein the color intensity is inversely proportional to the amount of unreacted dye.

* * * * *